United States Patent [19]

DeSalvo et al.

[11] 4,033,333

[45] July 5, 1977

[54] ELECTRODE ARRANGEMENT FOR TAKING ELECTROCARDIOGRAMS

[75] Inventors: Ernest J. DeSalvo, Teaneck, N.J.; Marco D. Zarlengo, New York, N.Y.

[73] Assignee: Combined Scientific Resources Corporation, Teaneck, N.J.

[22] Filed: Dec. 10, 1975

[21] Appl. No.: 639,368

[52] U.S. Cl. .................... 128/2.06 E; 128/DIG. 4
[51] Int. Cl.² .......................................... A61B 5/04
[58] Field of Search ............... 128/2.06 E, 2.06 R, 128/2.06 B, 2.1 E, DIG. 4

[56] References Cited

UNITED STATES PATENTS

| | | | |
|---|---|---|---|
| 2,549,836 | 4/1951 | McIntyre et al. | 128/DIG. 4 X |
| 3,380,445 | 4/1968 | Frasier | 128/2.06 E |
| 3,476,104 | 11/1969 | Davis | 128/2.06 E |

FOREIGN PATENTS OR APPLICATIONS

| | | | |
|---|---|---|---|
| 1,355,600 | 2/1964 | France | 128/2.06 E |

OTHER PUBLICATIONS

Takagi et al., "The Electrodes-Triangle," Amer. Heart J., Sept. 1970, pp. 427-428.

*Primary Examiner*—Robert W. Michell
*Assistant Examiner*—Lee S. Cohen
*Attorney, Agent, or Firm*—Gottlieb, Rackman & Reisman

[57] ABSTRACT

There is disclosed an electrode arrangement for taking electrocardiograms, suitable for use when limited information must be determined rapidly. The arrangement consists of a small rigid plate having four electrode posts mounted thereon. Three of the posts are secured in slots which extend radially outward from a fixed central post, the positions of the outer posts depending on whether the patient is an infant or an adult. In an emergency, the apparatus is simply pressed against the chest of a patient, and conventional ECG leads are attached to the posts. The right-leg lead is attached to the center post, and the left-leg, right-arm and left-arm leads are attached to the outer posts. Preferably, the arrangement is left permanently attached to the leads of an ECG machine so that, in case of an emergency, the set-up time (which includes the application of electrode jelly to the electrode posts) takes only several seconds. The outer contour of the plate has the general shape of a "Y" for fitting between the breasts of an adult female patient; this allows all of the posts to make good skin contact.

2 Claims, 3 Drawing Figures

ELECTRODE ARRANGEMENT FOR TAKING ELECTROCARDIOGRAMS

This invention relates to electrode arrangements for taking electrocardiograms, and more particularly to an arrangement which allows rapid set-up in case of an emergency.

When taking an electrocardiogram, electrodes must be attached to the patient. Electrode "jelly" is usually placed on the skin of the patient where the electrodes are to be attached, and electrode posts are then secured by straps. Thereafter, cables from the ECG machine are secured to the posts and a wide variety of waveforms may be recorded. Typically, the machine may have up to twelve "leads"; the machine allows up to twelve functions to be recorded with each function being dependent upon the potential between a pair of leads or several leads in combination. Although much information can be determined once the cables are in place, it usually takes several minutes to accomplish this.

In emergency situations, it is more important to secure a limited amount of information immediately than to secure a lot of information after a prolonged set-up time. For example, rate and rhythm must be known immediately, and accurate waveshapes are far less important. In the prior art, however, there has been no way to set up an ECG apparatus in a matter of seconds.

It is a general object of our invention to provide an electrode arrangement for taking electrocardiograms which permits a set-up time of only several seconds.

Briefly, in accordance with the principles of our invention, we provide a rigid non-conductive plate (typically, made of clear plastic) of a size suitable for placement on the chest of a patient. The plate has four electrode posts. Three of these are secured in slots which extend radially outward from a fixed central post. When using the electrode arrangement on an adult patient, the three outer posts are moved to their farthest positions from the center post. It is only when using the arrangement on an infant, when the separation between the adult post positions might prevent contact with the infant, that the three moveable posts are moved inwardly toward the center post. The slots are arranged such that when the center post is placed upon or immediately inferior to the zyphoid sternum, the upper two slots radiate toward the apices of the right and left shoulders. The third slot radiates downwardly from the center post. In the preferred embodiment of the invention, the angle between the two upper slots is 90°.

The right-leg cable from the ECG machine is attached to the center post. The left-arm and right-arm cables are attached to the left and right upper posts respectively, and the left-leg cable is attached to the bottom post. So that the device can be used in an emergency, the cables from the ECG machine should be left secured to the posts when the system is not in use. Thus to set up the apparatus, all that is required is to place some electrode jelly on the face of each of the four posts, and then to press the plate against the patient's chest so that the posts contact the skin of the patient.

The angular positions of the slots ensure that the relative positions of the electrode posts are correct for any patient, whether infant or adult. (To move the three adjustable posts within their respective slots requires only a few seconds.)

The resulting ECG traces are adequate for assessment of cardiac rate, rhythm and conduction system integrity. Because the electrodes are relatively close together, this being the necessary result of securing them on a small rigid plate to achieve rapid set-up, the system does not produce waveshapes which are the same as those which would be achieved were a conventional system utilized. For example, the resulting traces should not be used to diagnose morphological changes such as miocardial infarction or ventricular hypertrophy. But the arrangement does permit immediate determination of such things as rate, rhythm and intervals of a patient's electrocardiogram.

Although the center post should be placed upon or immediately inferior to the zyphoid sternum, the exact position of this post is of little importance since it serves primarily as a ground connection. Ideally, the two upper posts, corresponding to the right and left arm connections, should be placed at approximately the fourth intercostal space, and the bottom post should be as low as possible, i.e., separated to the maximum extend from the right and left arm electrodes. In practice, we have found that satisfactory results are obtained no matter what the position on the device on the patient, provided that the device is placed more or less in the center of the patient's chest. All of the standard and augmented leads may be sampled for the configuration best suited for diagnosis. It is preferable to apply firm pressure to the plate to ensure good contact with the skin of the patient.

The outer contour of the plate in the preferred embodiment of the invention has the shape of a "Y". This is the best shape for ensuring electrode post contact in the case of a female patient. The bottom leg of the plate (corresponding to the left-leg connection) fits between the breasts of the female patient. Because each of the upper legs extends outwardly from the center of the plate at an angle, the two upper legs are above the breasts of the patient rather than on top of them. In this way, all four posts may make electrical contact with the skin of the patient though they are contained in a rigid plate.

Further objects, features and advantages of our invention will become apparent upon consideration of the following detailed description in conjunction with the drawing, in which.

Figure 1:
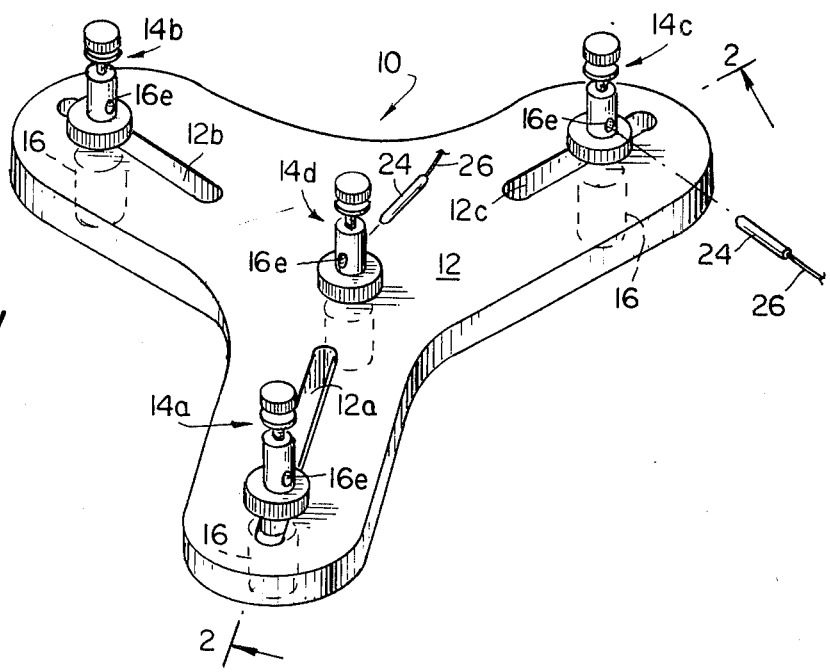
FIG. 1 is a perspective view of the preferred embodiment of our invention.

Electrode arrangement 10 includes a rigid, non-conductive plate 12 and four electrode posts 14a–14d. The plate has the general shape of "Y" and the four posts are secured in the plate. Post 14d is secured at the center of the plate and is fixed in position. Three slots 12a, 12b and 12c radiate from the central post. The angle between slots 12b and 12c is 90°, and the angle between each of these slots and slot 12a is 135°. Posts 14a, 14b and 14c are mounted in respective slots 12a, 12b and 12c.

When placing the device on the chest of a patient, slot 12a extends downwardly from the center of the patient's chest toward his legs. In this position, slots 12b and 12c radiate upwardly toward the left and right shoulders respectively.

A typical cable 26 from an ECG machine terminates in a pin 24. As will be described with reference to FIGS. 2 and 3, the pin in each of four cables is attached to a respective post. The right-leg cable from the ECG machine is attached to central post 14d and the left-leg cable is attached to post 14a. The left-arm and right-arm cables are attached respectively to posts 14b and 14c.

Although an angle of 90° is preferred between slots 12b and 12c, we have found that adequate results can be obtained if the angle varies between 80–100°. No matter what the angle, slot 12a should be symmetrical relative to the other two slots. The minimum distance between the inner ends of slots 12b and 12c, and center post 12d, should be approximately 1 inch. If the posts corresponding to the left-arm and right-arm connections are too close to the (ground) center post, the results are in some cases not satisfactory. The inner end of slot 12a can be as close as .25 inch from the center post. As for the outer ends of the three slots, there is no "maximum" limit, although obviously there is no need to have slots which extend out past the patient. In practice, we have found that there is no need for the outer end of each slot to be more than 6 inches away from the center post. Whenever the device is used, it is desirable to separate the moveable posts as far as possible from one another, i.e., each of the posts should be at the outer end of its respective slot provided that in such a position contact is maintained with the patient. Since most emergencies involve adult patients, the posts should be maintained in their outermost positions, with the cables attached. Thus to set up the system, all that is required is to place some electrode jelly at the bottom of each post and to then hold plate 12 firmly against the patient's chest.

In the preferred embodiment of the invention, the outer contour of plate 12 has the shape of a "Y". The leg which contains slot 12a corresponds to the bottom of the Y, and the two other legs correspond to the upper legs of the Y. As described above, this arrangement ensures the best possible skin contact even in the case of a female patient. Although the two legs containing slots 12b and 12c are separately identifiable, the top of the unit need not be dished out as in the illustrative embodiment of the invention. Instead, the plate may have a straight edge at the top, the overall shape thus being a triangle with a leg depending from the bottom corner. The important contour is that between the legs containing slots 12a and 12b, and the legs containing slots 12a and 12c. It is this Y-shaped outer contour which is best adapted for use with female patients.

Figure 2:
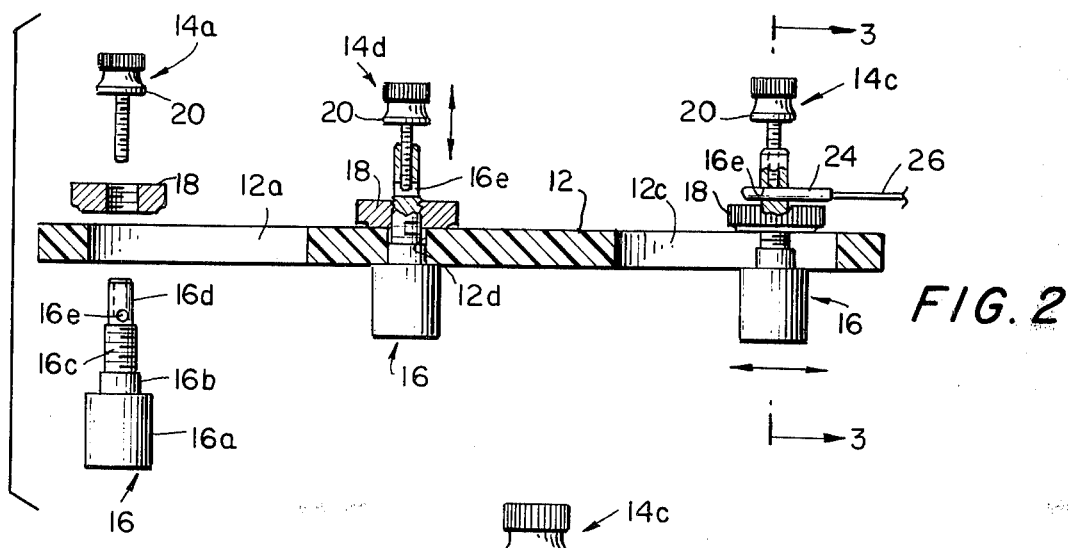
FIG. 2 is a sectional view through the line 2—2 of FIG. 1.

In FIG. 2, post 14a is shown disassembled and posts 14d and 14c are shown in place. The disassembled post illustrates the three-part construction of each post. The bottom part 16 has a large cylindrical section 16a which makes contact with the skin of the patient and a smaller cylindrical section 16b which fits within the respective slot in plate 12. Screw threaded section 16c extends upwardly from section 16b, and finally a smaller-diameter section 16d extends upwardly at the top of the element. A hole 16e extends through part 16d, and a screw thread is provided internally to part 16d.

In assembling the post, part 16 is pushed upwardly, and nut 18 is tightened around screw threaded section 16c, as seen most clearly in the two assembled posts shown in FIG. 2. Screw 20 extends downwardly through nut 18 into the internal threaded hole in section 16d. When a pin 24 is inserted through hole 16e in one of the posts, screw 20 is tightened against the top of the pin as seen most clearly in the right-most post 14c of FIG. 2. The attachment of a cable to a respective post is accomplished rapidly simply by inserting a pin 24 through the respective hole 16e and then tightening the respective screw 20. Similarly to move a post within its respective slot, all that is necessary is to loosen nut 18, to move the post assembly, and then to tighten the nut.

Figure 3:
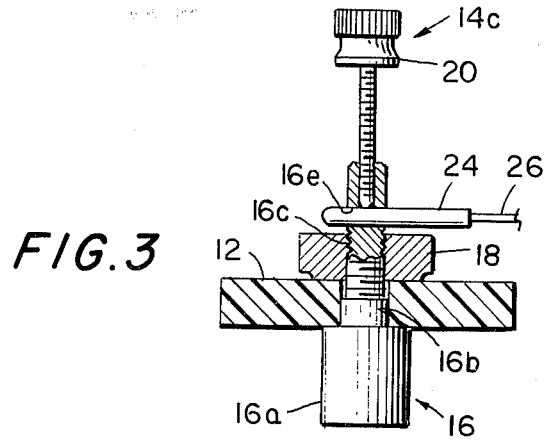
FIG. 3 is an enlarged sectional view through the line 3—3 of FIG. 2.

FIG. 3 is an enlarged view of an electrode assembly and best illustrates the manner in which the three parts of the assembly cooperate with one another.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What we claim is:

1. An electrode arrangement for use in the taking of electrocardiograms comprising a rigid nonconductive plate having three slots extending radially outward from the center thereof; a first electrode post fixed in the center of said plate; second, third and fourth electrode posts each mounted for movement within a respective one of said slots, each of said moveable electrode posts including means for enabling said post to be moved within its respective slot and to be secured in a desired position; all of said electrode posts projecting outwardly from one side of said plate for connection to electrocardiographic machine cables and projecting outwardly from the other side of said plate for contacting the skin of a patient; and means in each of said electrode posts on that part thereof which projects outwardly from said one side of said plate for securing thereto a cable from an electrocardiographic machine; the angle between a first and second slot being in the range 80–100°, the third slot being symmetrically disposed relative to said first and second slots, and two edges of said plate having the general contour of the left and right edges of a Y.

2. An electrode arrangement in accordance with claim 1 wherein the distance between the inner end of each of said first and second slots and said first electrode post is at least one inch, and the distance between the inner end of said third slot and said first electrode post is at least 0.25 inch.

* * * * *